United States Patent
Grant (10) Patent No.: US 8,231,388 B2
(45) Date of Patent: Jul. 31, 2012

(54) DENTAL IMPLANT (75) Inventor: James C. Grant, Colorado Springs, CO (US)

(73) Assignee: Grant Dental Technology Corporation, Colorado Springs, CO (US)

( * ) Notice: Subject to any disclaimer, the term of this patent is extended or adjusted under 35 U.S.C. 154(b) by 307 days.

(21) Appl. No.: 12/243,676

(22) Filed: Oct. 1, 2008

(65) Prior Publication Data

US 2009/0226857 A1  Sep. 10, 2009

Related U.S. Application Data (63) Continuation-in-part of application No. 12/074,524, filed on Mar. 4, 2008, now Pat. No. 7,806,685.

(51) Int. Cl.
*A61C 8/00* (2006.01)
(52) U.S. Cl. ...................................................... 433/174
(58) Field of Classification Search .......... 433/172–176, 433/201.1, 202.1, 215, 220, 221; 606/280, 606/70–71, 281–299, 86 B
See application file for complete search history.

(56) References Cited

U.S. PATENT DOCUMENTS

| | | | |
|---|---|---|---|
| 4,086,701 A | 5/1978 | Kawahara et al. | |
| 5,040,982 A | 8/1991 | Stefan-Dogar | |
| 5,297,963 A | 3/1994 | Dafatry | |
| 5,513,989 A | 5/1996 | Crisio | |
| 5,564,925 A | 10/1996 | Shampanier | |
| 5,591,029 A | 1/1997 | Zuest | |
| 5,810,592 A | 9/1998 | Daftary | |
| 6,068,479 A | 5/2000 | Kwan | |
| 6,120,292 A | 9/2000 | Buser et al. | |
| 6,168,436 B1 | 1/2001 | O'Brien | |
| 6,250,922 B1 | 6/2001 | Bassett et al. | |
| 6,287,117 B1 | 9/2001 | Niznick | |
| 6,454,569 B1 | 9/2002 | Hollander et al. | |
| 6,537,069 B1 | 3/2003 | Simmons, Jr. | |
| 6,843,653 B2 | 1/2005 | Carlton | |
| 6,863,529 B2 | 3/2005 | Strong et al. | |
| 7,056,117 B2 * | 6/2006 | Simmons, Jr. | 433/173 |
| 7,097,451 B2 | 8/2006 | Tang | |
| 7,101,177 B2 | 9/2006 | Lin | |
| 7,806,685 B1 | 10/2010 | Grant | |
| 2002/0076673 A1 * | 6/2002 | Wagner et al. | 433/173 |
| 2004/0265781 A1 | 12/2004 | Coatoam | |
| 2006/0014120 A1 | 1/2006 | Sapian | |
| 2008/0118892 A1 | 5/2008 | Adams | |
| 2008/0124675 A1 | 5/2008 | Adams | |

(Continued)

OTHER PUBLICATIONS

Plate. (n.d.). Dictionary.com Unabridged. Retrieved Dec. 1, 2010, from Dictionary.com website: http://dictionary.reference.com/browse/plate.*

(Continued)

*Primary Examiner* — Heidi M Eide
(74) *Attorney, Agent, or Firm* — Kilpatrick Townsend & Stockton LLP (57) ABSTRACT

A tooth implant assembly has a base plate, a base attachment fastener, a collar, a crown attachment fastener, and a tooth crown. The base plate has a central opening and a coronal surface. The base attachment fastener is adapted for insertion into and engagement with the central opening in the base plate. The base attachment fastener also has a head with a central bore extending longitudinally into the head. The crown attachment fastener has a threaded distal end adapted for threaded engagement with the central bore of the base attachment fastener.

16 Claims, 7 Drawing Sheets

U.S. PATENT DOCUMENTS

| | | |
|---|---|---|
| 2009/0258329 A1 | 10/2009 | Adams |
| 2010/0159419 A1 | 6/2010 | Grant |
| 2010/0266987 A1 | 10/2010 | Ford |
| 2010/0330534 A1 | 12/2010 | Hyun |
| 2011/0151408 A1 | 6/2011 | Grant |

OTHER PUBLICATIONS

Stud. (n.d.). Dictionary.com Unabridged. Retrieved Apr. 20, 2011, from Dictionary.com website: http://dictionary.reference.com/browse/stud.*

Teeth. (n.d.). Dictionary.com Unabridged. Retrieved Apr. 20, 2011, from Dictionary.com website: http://dictionary.reference.com/browse/teeth.*

PCT International Search Report and Written Opinion mailed Feb. 19, 2009; International Application No. PCT/US2009/034477, 14 pages.

International Search Report and Written Opinion of PCT/US2011/022737 mailed on Mar. 23, 2011, 11 pages.

* cited by examiner

DENTAL IMPLANT

CROSS REFERENCE

This application is a continuation in part of U.S. Application Serial No. 12/074,524, filed on Mar. 04, 2008, now U.S. Pat. No. 7,806,685, issued Oct. 15, 2010.

BACKGROUND

Implants are popular means of replacing a lost tooth. Due to their relatively low maintenance and durability people often prefer implants to bridges. Nevertheless, there is a largely undocumented body of complaints voiced to front line dentists about implants, by their patients. These complaints generally are about food impacting and accumulating around and beneath the crown portion of the implant in the enlarged periodontal gap between the implant and the adjacent teeth.

The following is a discussion and description of specific embodiments of this invention, such being made with reference to the drawings, wherein the same reference numerals are used to indicate the same or similar parts and/or structure. It should be noted that such discussion and description is not meant to unduly limit the scope of the invention.

DETAILED DESCRIPTION

Figure 1:
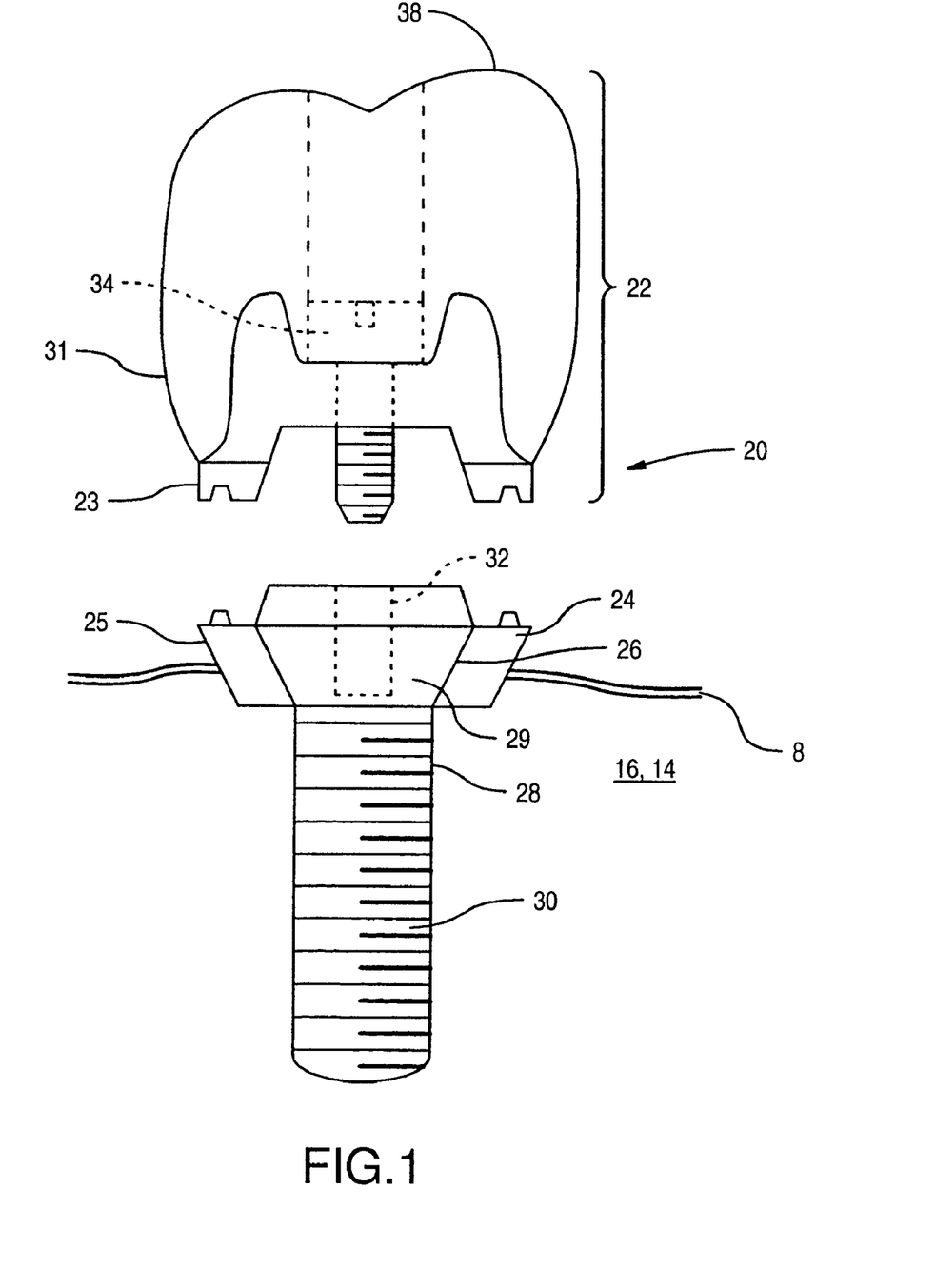
FIG. 1 is a side elevation diagram of an implant having an enlarged base seated directly on the jaw.

FIG. 1 is a side elevation diagram of an improved tooth implant assembly or prosthesis 20 having a base 24 for seating on jaw 16. In one embodiment, tooth implant assembly 20 includes base plate 24, base attachment fastener 28, crown attachment fastener 34, crown supporting means 36 (FIG. 2), and tooth crown 38.

Generally, the improved tooth implant 20 comprises: i) a crown portion 22 having a lower portion 23 adapted for seating and connection; ii) a base 24 having an upper portion adapted to matably receive the crown portion 22, a lower portion adapted to seat directly on the bone 14 of one of the jaws 16, said base 24 having an upright, or central, opening 26 therethrough; and, iii) a base attachment fastener 28 having a head 29 adapted to be seated on and around upright opening 26, and a threaded end portion, or shaft, 30 for screwable reception in the jaw 16 to thereby anchor the base 24 thereon. The base 24 of the implant 20 is enlarged to better distribute load on the jaw 16 and thereby additionally allow said crown portion 22 to have more upright peripheral sidewalls 31, so that embrasures, or periodontal gaps, 12 (FIGS. 3-7) between the bottom portion of the crown portion and adjacent teeth 10 (FIGS. 3-7) are thereby substantially reduced, and so that both food impaction and collection therein is also substantially reduced. In one embodiment, the base 24 is generally rectangular and non-rotatable.

Base attachment fastener 28 is adapted for insertion into and engagement with central opening 26 in base plate 24. In one embodiment, base attachment fastener 28 is a self tapping screw. In one embodiment, base attachment fastener 28 is a bone screw.

Base attachment fastener 28 has head 29 with central bore 32 formed longitudinally in head 29 of fastener 28. In one embodiment, central bore 32 of base attachment fastener 28 extends into threaded shaft 30. In one embodiment, head 29 of base attachment fastener 28 is a countersink head adapted to fit countersunk central opening 26.

Within this specification "jaw" 16 is intended and defined to include either the upper jaw or the lower jaw. Similarly, within this specification "bone" 14 is intended and defined to include either the maxilla or the mandible.

If the base 24 is sized generally similarly to the bottom portion of a removed tooth (not shown) then the periodontal gaps 12 on opposite sides of the implanted crown portion 22 will not be enlarged. The base 24 may be further enlarged to maximally minimize the periodontal gaps 12 between the implant 20 and adjacent teeth 10.

In one embodiment of the invention, the base 24 has a sloping peripheral sidewall 25 and wherein the bottom side portion is smaller in area than the top side portion thereof. The bottom side portion of the base 24 may be embedded within the bone 14 of the jaw 16. Alternatively, if bone 14 strength is an issue, the bottom side portion of the base 24 may be generally fitted to the vertical curvature of the bone 14 of the jaw 16.

In another embodiment of the invention, the peripheral sidewall 25 of the base 24 is coated or roughened to facilitate gum 8 adhesion thereto. In one embodiment, the upper portion of the base attachment fastener 28 comprises an internally threaded hole, or central bore, 32 for reception of a crown attachment bolt 34. It is also contemplated that the top portion of the base 24 and the bottom side portion of the crown 22 are matingly configured to ensure proper and non-rotatable alignment of the crown portion 22 on the base 24.

Figure 2:
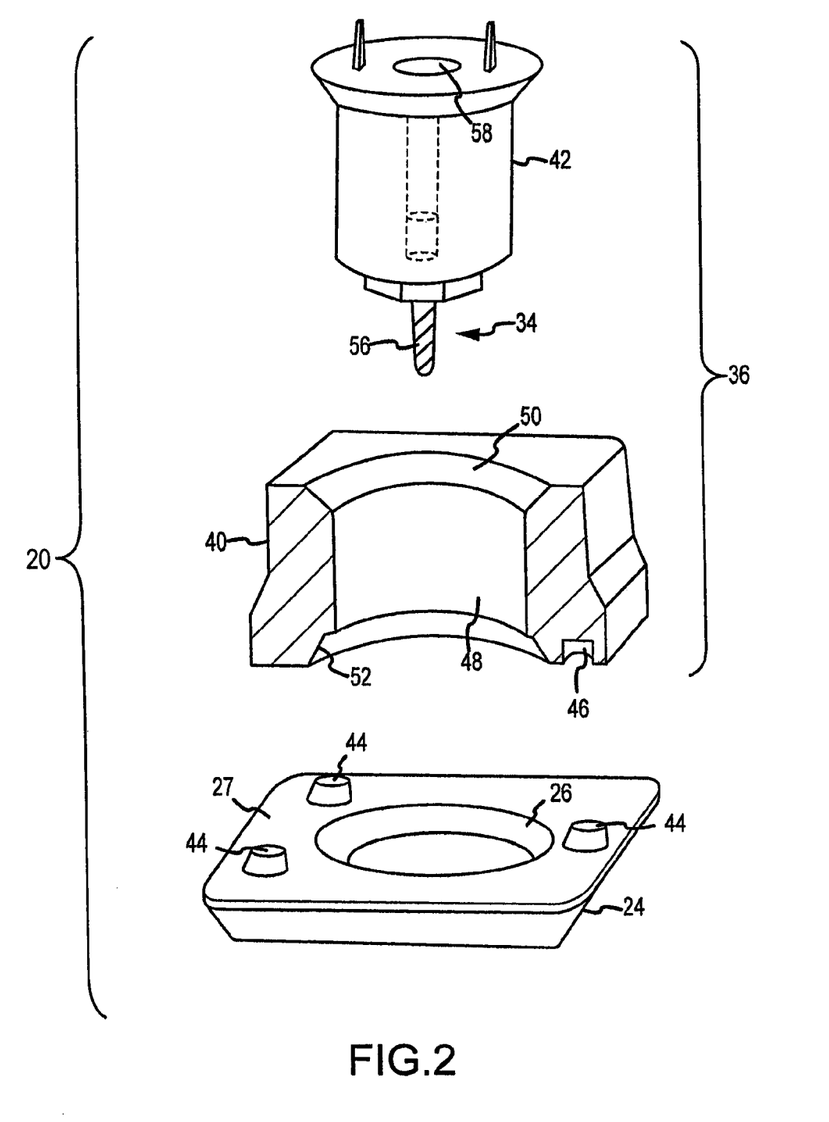
FIG. 2 is an exploded view of the base plate and crown supporting means of the implant.

FIG. 2 is a more detailed illustration of the base plate 24 and crown support means 36 of implant 20. Tooth crown 38 is supported by and attached to crown supporting means 36. Together tooth crown 38, crown supporting means 36, and crown attachment screw 34 embody crown portion 22.

Base plate 24 has central opening 26 and coronal surface 27. The terms "coronal" and "apical" are used in this specification to describe the side of a structure closest to the crown and apex (root), respectively, of a tooth.

In one embodiment, central opening 26 of base plate 24 is countersunk. Central opening 26 may be beveled at any angle, even a concave angle, or it may be straight with no bevel. In one embodiment, coronal surface 27 is a flat surface. In one embodiment, coronal surface 27 of base plate 24 includes teeth means 44 for engagement, such as a plurality of upstanding studs 44.

Crown supporting means 36 carries crown attachment fastener 34. Crown supporting means 36 is disposed on coronal surface 27 of base plate 24. In one embodiment, crown support means 36 includes means 46 for engaging teeth means 44 or upstanding studs 44 of coronal surface 27.

In one embodiment, crown support means 36 includes collar 40 and cylindrical insert 42. Collar 40 is shown partially cut away in FIG. 2.

Collar 40 includes longitudinal opening 48 with coronal 50 and apical 52 edges. Collar 40 is disposed on coronal surface 27 of base plate 24.

Cylindrical insert 42 is disposed within collar 40 and supported by coronal edge 50 of collar 40. Cylindrical insert 42 has a longitudinal channel 58 formed therein for carrying crown attachment fastener 34.

Crown attachment fastener 34 is adapted for threaded engagement with central bore 32 of base attachment fastener 28. In one embodiment, Crown attachment fastener 34 has a threaded shaft 56 adapted for threaded engagement with central bore 32.

Generally, the method of implanting a tooth implant or prosthesis 20 in a jaw 16 comprises the following steps: i) providing a tooth implant 20 as most generally described above; ii) drilling a pilot hole 6, sized to accommodate the internal diameter of the base attachment screw 28, said hole 6 laterally centered in the jaw 16 between adjacent teeth 10 in a open space left by a removed tooth (not shown); iii) removing sufficient gum 8 to allow the base 24 to seat directly on the bone 14 of the jaw 16, and thereafter positioning the threaded end portion 30 of the base attachment screw 28 through the upright opening 26 in the base 24 and screwing said screw 28 into the bone 14 of the jaw 16 thereby attaching the base 24 to the jaw 16; iv) thereafter positioning, fitting and maintaining the removed gum 8 peripherally around the base 24 attached to the jaw 16; v) molding a crown portion 22 having a bottom portion sized to fit on the base 24 and having a top portion sized appropriately to fill the open space between the adjacent teeth 10; and, vi) finally attaching the molded crown portion 22 to the base 24 anchored on the jaw 16. The base 24 of the implant 20 is enlarged to better distribute load on the jaw 16, so that periodontal gaps 12 between the bottom portion of the crown portion 22 and adjacent teeth 10 are thereby reduced, and so that both food impaction and collection therein is minimal. This most general method may be detailed with the apparatus limitations specified above under the most general description of the tooth implant 20.

FIG. 3-7 illustrate an embodiment for installing a tooth implant in a jaw 16 having bone 15 and gum 8. Although the steps represented in FIGS. 3-7 are presented in a specific order, the technology presented herein can be performed in any variation of this order. Furthermore, additional steps may be executed between the steps illustrated in FIGS. 3-7

Figure 3:
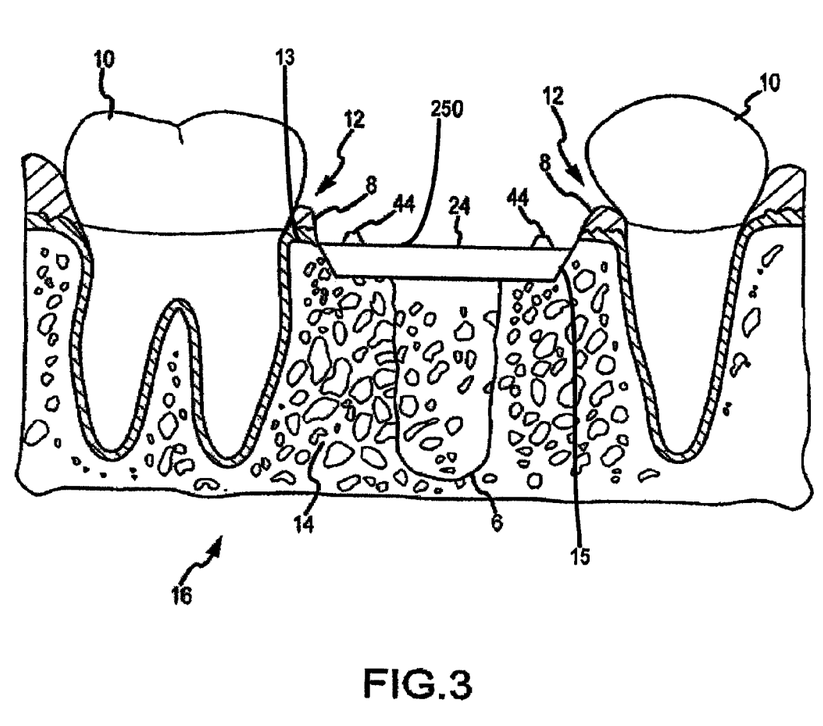
FIGS. 3-7 illustrate an embodiment of steps in a method for installing the tooth implant of FIG. 1.
Figure 4:
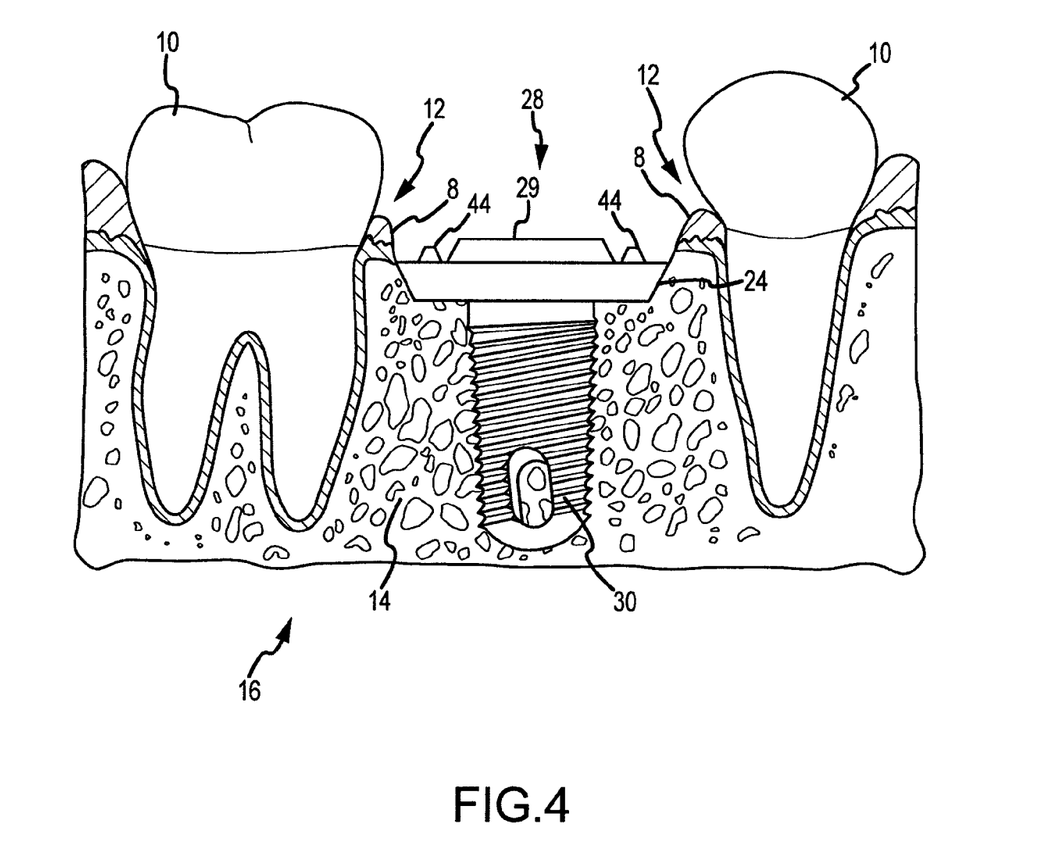
Figure 5:
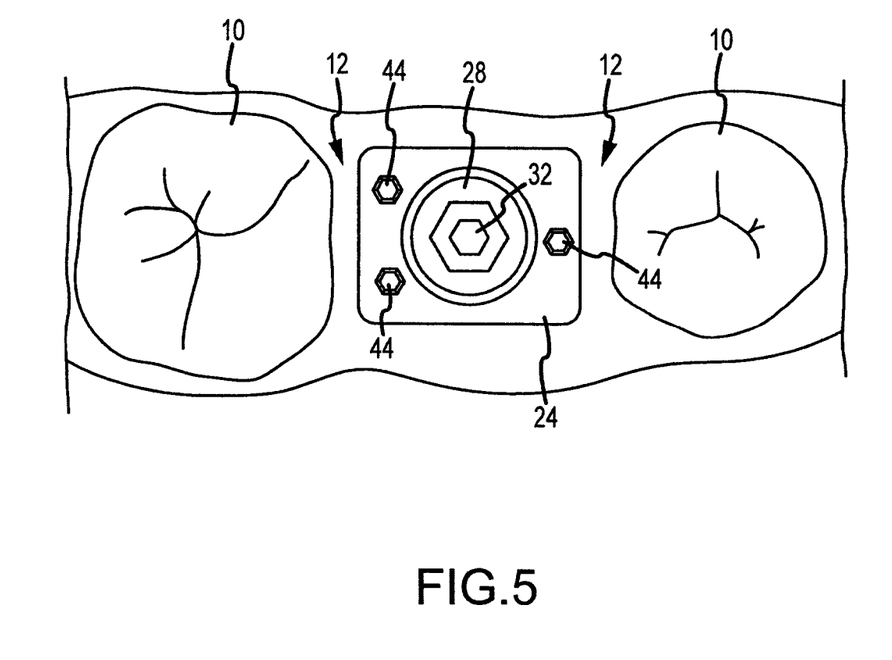

FIGS. 3 and 4 are side elevations of base plate 24 being fastened to jaw 16. FIG. 5 is a top elevation of the step shown in FIG. 4.

In one embodiment, fastening base plate 24 to jaw 16 includes drilling a pilot hole 6, removing gum 8 from jaw 16, and positioning threaded shaft 30 of base attachment screw 28 through central opening 26.

Pilot hole 6 is drilled, sized to accommodate the internal diameter of base attachment screw 28. Pilot hole 6 is laterally centered in jaw 16.

Sufficient gum 8 is removed from jaw 16 to allow base plate 24 of implant 20 to seat directly on bone 14 of jaw 16. As shown in FIG. 3, bone 14 of jaw 16 includes a recessed region 15 for receiving base plate 24. Recessed region 15 is recessed in bone 14 such that a top surface 250 of base plate is slightly above or slightly below a top surface 13 of bone 14. Also, the majority of base plate 24 is shown embedded within bone 14 below top surface 13 of bone 14. Threaded shaft 30 of base attachment screw 28 is then positioning through central opening 26 in base 24 of implant 20. Screw 28 is screwed into bone 14 of jaw 16 thereby attaching base plate 24 to jaw 16.

Figure 6:
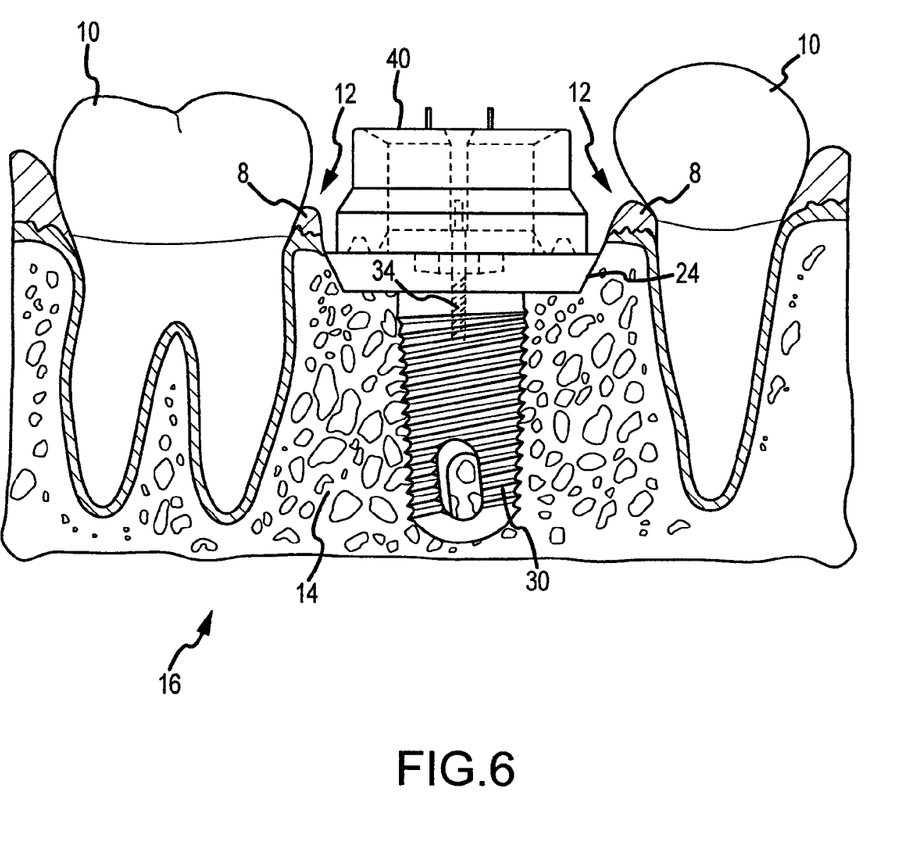
Figure 7:
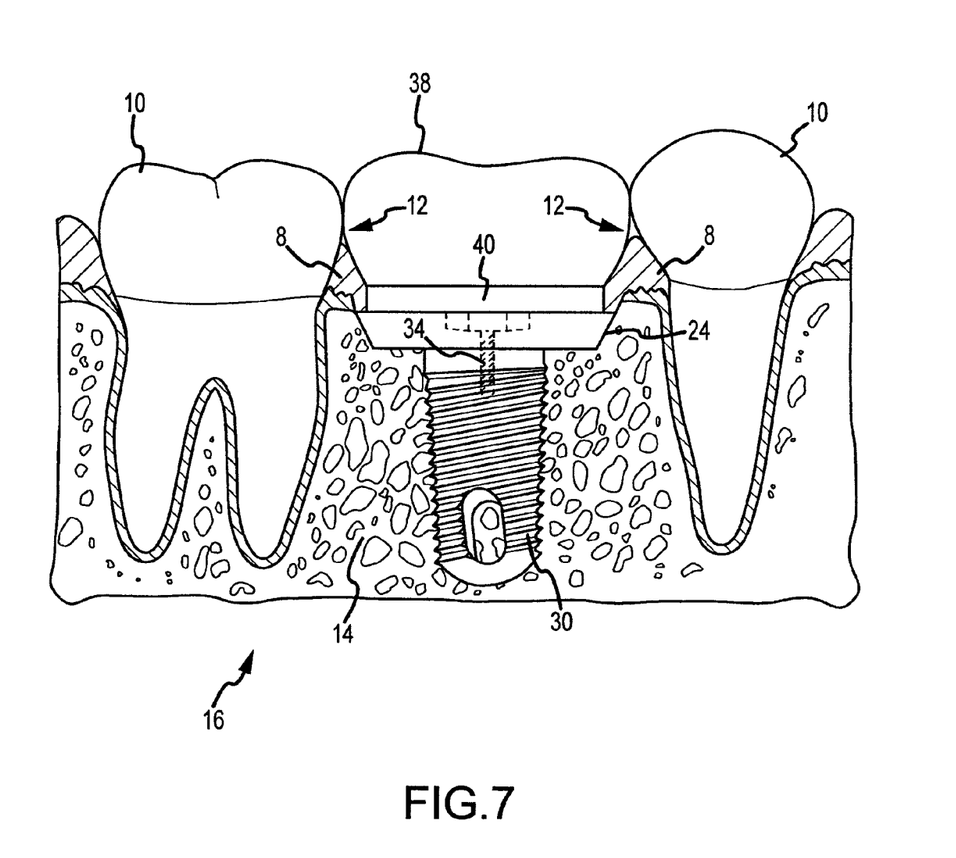

FIG. 6 is a side elevation showing collar 40 being affixed to base plate 24. Longitudinal opening 48 is provided in collar 40. Collar 40 is disposed on coronal surface 27 of base plate 24. Crown attachment fastener 34 is inserted through collar 40. Cylindrical insert 42 is disposed within collar 40. FIG. 7 is a side elevation showing tooth crown 38 being attaching to collar 40.

The foregoing description is only illustrative of the invention and not intended to be exhaustive or to limit the invention to the precise forms disclosed. Various alternatives and modifications can be devised by those skilled in the art without departing from the invention. Accordingly, the present invention embraces all such alternatives, modifications, and variances that fall within the scope of the appended claims.

What is claimed is:

1. A tooth implant assembly comprising:
   a base plate having a central opening and a flat coronal surface, wherein the base plate has a bottom surface and sides that extend from the coronal surface to the bottom surface, and wherein the base plate is configured to be placed within a recess in a patient's jawbone such that a majority of the base plate is embedded within the patient's jawbone;
   a base attachment fastener adapted for insertion into and engagement with the central opening in the base plate and having a head with a central bore formed longitudinally in the head of the base attachment fastener;
   a crown attachment fastener adapted for threaded engagement with the central bore of the base attachment fastener;
   a crown support that is adapted to be disposed on the coronal surface of the base plate, wherein the crown support has a bottom surface that is adapted to be placed against the coronal surface of the base plate, and wherein the crown support defines a through hole that is aligned with a central axis of the crown support; and
   a sleeve that is adapted to be positioned within the through hole of the crown support, wherein the sleeve defines a cylindrical opening that is aligned with the central bore of the base plate;
   a tooth crown supported by the crown support.

2. The tooth implant assembly of claim 1 wherein:
   the coronal surface of the base plate includes teeth means for engagement and the crown support includes means for engaging the teeth means of the coronal surface.

3. The tooth implant assembly of claim 1 wherein:
   the coronal surface of the base plate includes a plurality of upstanding studs and
   the crown support includes means for engaging the upstanding studs.

4. The tooth implant assembly of claim 1 wherein the base attachment fastener is a self tapping screw.

5. The tooth implant assembly of claim 1 wherein the base attachment fastener includes a bone screw.

6. The tooth implant assembly of claim 1 wherein:
   the base attachment fastener includes a threaded shaft and the central bore of the base attachment fastener extends into the threaded shaft.

7. The tooth implant assembly of claim 1 wherein:
   the central opening of the base plate is countersunk and the head of the base attachment fastener is a countersink head adapted to fit the countersunk central opening.

8. A tooth implant assembly comprising:
   a base plate having a central opening and a flat coronal surface, wherein the base plate has a bottom surface and sides that extend from the coronal surface to the bottom surface, and wherein the base plate is configured to be placed within a recess in a patient's jawbone such that a majority of the base plate is embedded within the patient's jawbone,
   a base attachment fastener adapted for insertion into and engagement with the central opening in the base plate and having a head with a central bore extending longitudinally into the head of the fastener;
   a collar having a longitudinal opening with a coronal edge and an apical edge, the collar disposed on the coronal surface of the base plate such that the apical edge contacts the coronal surface of the base plate;

a crown attachment fastener having a threaded distal end adapted for threaded engagement with the central bore of the base attachment fastener;

a cylindrical insert disposed within the collar, the insert having a longitudinal channel formed therein for receiving the crown attachment fastener; and a tooth crown supported by and attached to the collar.

9. The tooth implant assembly of claim 8 wherein:
the coronal surface of the base plate includes teeth means for engagement and the collar includes means for engaging the teeth means of the coronal surface.

10. The tooth implant assembly of claim 8 wherein:
the coronal surface of the base plate includes a plurality of upstanding studs and the collar includes means for engaging the upstanding studs.

11. The tooth implant assembly of claim 8 wherein the base attachment fastener is a self tapping screw.

12. The tooth implant assembly of claim 8 wherein the base attachment fastener includes a bone screw.

13. The tooth implant assembly of claim 8 wherein:
the base attachment fastener includes threaded shaft and the central bore of the base attachment fastener extends into the threaded shaft.

14. The tooth implant assembly of claim 8 wherein:
the central opening of the base plate is countersunk and the head of the base attachment fastener is a countersink head adapted to fit the countersunk central opening.

15. The tooth implant assembly of claim 8 wherein the coronal edge is chamfered.

16. The tooth implant assembly of claim 8 wherein the apical edge is chamfered to engage the head of the base attachment fastener.

* * * * *